United States Patent
Cross, Jr. et al.

(10) Patent No.: US 7,601,879 B2
(45) Date of Patent: Oct. 13, 2009

(54) PARAFFIN ALKYLATION

(75) Inventors: William M. Cross, Jr., Houston, TX (US); Lawrence A. Smith, Jr., Houston, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 152 days.

(21) Appl. No.: 11/505,029

(22) Filed: Aug. 16, 2006

(65) Prior Publication Data

US 2008/0045763 A1    Feb. 21, 2008

(51) Int. Cl.
*C07C 2/54* (2006.01)
*C07C 2/04* (2006.01)

(52) U.S. Cl. .................. 585/332; 585/331; 585/903

(58) Field of Classification Search .............. 585/332, 585/331, 903
See application file for complete search history.

(56) References Cited

U.S. PATENT DOCUMENTS

| | | | | |
|---|---|---|---|---|
| 3,835,199 | A * | 9/1974 | Schwartz et al. | 585/630 |
| 4,200,714 | A * | 4/1980 | Mahoney et al. | 526/68 |
| 4,254,294 | A * | 3/1981 | Juguin et al. | 585/525 |
| 4,301,315 | A * | 11/1981 | Haskell et al. | 585/304 |
| 6,194,625 | B1 | 2/2001 | Graves et al. | |
| 6,395,945 | B1 | 5/2002 | Randolph | |
| 6,858,770 | B2 | 2/2005 | Smith, Jr. et al. | |
| 6,995,296 | B2 | 2/2006 | Smith, Jr. et al. | |

OTHER PUBLICATIONS

PCT International Search Report issued in PCT Application No. PCT/US2007/076028 dated Jan. 11, 2008 (4 pages).
PCT Written Opinion issued in PCT Application No. PCT/US2007/076028 dated Jan. 11, 2008 (6 pages).

* cited by examiner

*Primary Examiner*—Thuan Dinh Dang
(74) *Attorney, Agent, or Firm*—Osha Liang LLP

(57) ABSTRACT

A process for paraffin alkylation of isoalkane with isoolefins in which an olefin component comprising oligomerized propylene, oligomerized isoolefin or mixtures thereof is fed to a paraffin alkylation unit wherein the dissociated olefin components forming the oligomers react with isoalkane to produce a reaction mixture containing an alkylate and unreacted isoalkane The reaction mixture is fractionally distilled to recover unreacted isoalkane as overheads and alkylate as bottoms. The stoichiometry of isoolefins to isoalkane in the alkylation unit is maintained by adjustment of the feed to the oligomerization, for example, by adding fresh isoalkane to the recovered, unreacted isoalkane from the alkylation unit being recycled to the oligomerization. Alternatively, a portion of the recovered unreacted isoalkane is dehydrogenation to an isoolefin which is added to the oligomerization.

15 Claims, 1 Drawing Sheet

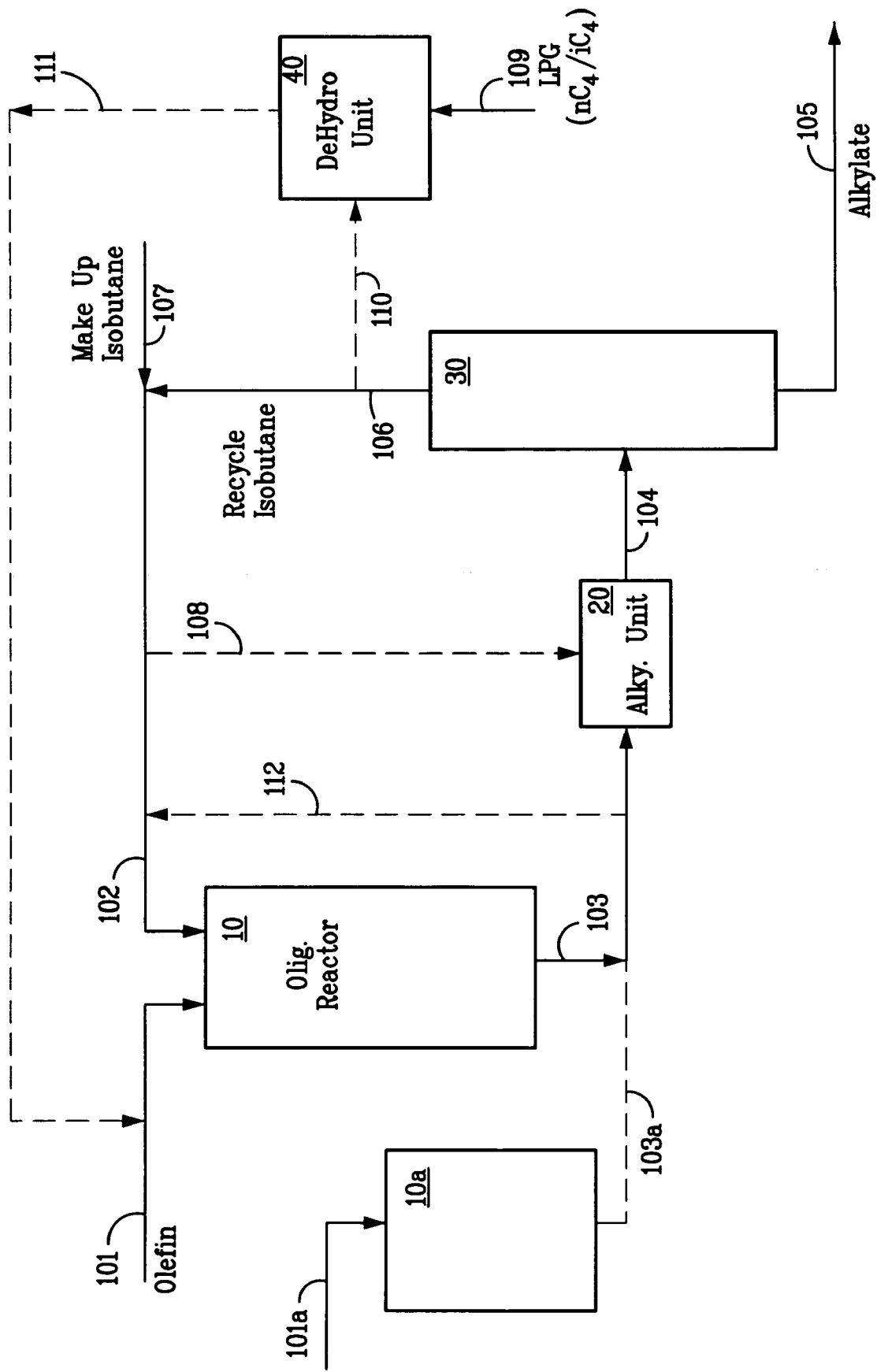

PARAFFIN ALKYLATION

BACKGROUND OF THE INVENTION

1. Field of the Invention

The present invention relates to the alkylation of paraffinic hydrocarbon feed stocks. More particularly the invention relates to a process for wherein the olefin feed is produced by the oligomerization of propylene and isoolefins. More particularly the invention relates to a process wherein a portion or all of the traditional isobutane paraffin feed/recycle is passed through the oligomerization reactor to act as a heat sink to remove part of the heat of reaction.

2. Related Information

U.S. Pat. No. 6,995,296 discloses a process for the alkylation of alkane with olefin or olefin precursor such as an oligomer of tertiary olefin comprising contacting a liquid system comprising acid catalyst, isoparaffin and olefin in concurrent downflow into contact in a reaction zone with a disperser mesh under conditions of temperature and pressure to react said isoparaffin and said olefin to produce an alkylate product. Preferably, the liquid system is maintained at about its boiling point in the reaction zone. Unexpectedly, the olefin oligomers have been found to function as olefin precursors and not as olefins in the reaction. The olefin precursor is preferably an oligomer comprising $C_8$ to $C_{16}$ olefins corresponding to oligomer prepared from $C_3$ to $C_5$ olefin. In a preferred embodiment the oligomer has 6 to 16 carbon atoms and corresponds to oligomers which are prepared from $C_4$ to $C_5$ olefins. Instead of the expected reaction between the oligomer and the isoalkane, the oligomer is cracked into its olefin components which react with the isoalkane on a molar basis.

The great advantage of the using oligomer olefin precursors for the paraffin alkylation is that although acid alkylations are extremely exothermic and require substantial refrigeration to maintain the reaction temperature in optimum range to prevent side reactions, the present reaction of the oligomers with the isoalkane to produce the alkylate in the same yields required less refrigeration making the process less expensive for the same yield of useful product. The oligomerization process produces a heat of reaction that does not require the magnitude of heat removal as in the cold acid process.

The widest use of the paraffin alkylation is for the preparation of a $C_8$ gasoline component. The feed to this process is usually a $C_4$ olefin component and tertiary butane in a "cold acid" reaction usually with sulfuric acid or HF acid.

SUMMARY OF THE INVENTION

The present invention is a process for the alkylation of isoalkane with an olefin under alkylation conditions in an alkylation unit, wherein the improvement is the adjustment of the feed to the oligomerization reactor to maintain the stoichiometry of olefin component to isoalkane in said alkylation unit. As used herein the term olefin component is understood to mean "oligomerized propylene, oligomerized isoolefin or mixtures thereof"

The present invention includes the operation of a paraffin alkylation of isoalkane with an olefin component comprising an oligomerization unit in which propylene or an isoolefin is reacted to provide oligomeric olefinic precursor effluent as feed to a paraffin alkylation unit wherein the olefin forming the oligomers of propylene and isoolefin react with isoalkane to produce a reaction mixture containing an alkylate, preferably corresponding to the alkylation product of the propylene or isoolefins with the isoalkane, and un reacted isoalkane to form a reaction mixture which is fractionally distilled in a distillation unit wherein unreacted isoalkane is separated from alkylate product. The improvement is the adjustment of the feed to the oligomerization unit to maintain the stoichiometry of propylene or isoolefins to isoalkane in said paraffin alkylation unit.

The recovered unreacted isoalkane may be used to maintain the stoichiometry of the propylene or isoolefins to isoalkane by (1) adding the unreacted isoalkane to the isoalkane recycle to the oligomerization unit from the distillation column or (2) by dehydrogenation of a portion of the unreacted isoalkane from the distillation column to an isoolefin product and addition of the isoolefin product to the propylene/isoolefin feed or a combination of (1) and (2). By making the adjustment to the oligomerization reaction, the added isoalkane and to a lesser extent the dehydrogenated isoalkane provide additional heat sink to control the temperature of the oligomerization as well as maintaining the reaction stoichiometry. An additional heat sink may be obtained by recycling a portion of the oligomeric olefinic precursor effluent from the oligomerization unit to the oligomerization unit.

BRIEF DESCRIPTION OF THE DRAWING

The FIGURE is a schematic representation of a several optional or concomitant embodiments of the invention.

DETAILED DESCRIPTION OF THE INVENTION

Preferably, the oligomer comprises $C_6$ to $C_{16}$ olefins corresponding to oligomer prepared from $C_3$ to $C_5$ olefins. In a preferred embodiment the oligomer has 6 to 16 carbon atoms and corresponds to oligomers which are prepared from $C_4$ to $C_5$ olefins.

The oligomerization of the tertiary olefin is also a preferred reaction when carried out on a naphtha stream with the separation of normal olefin being easily achieved by fractionation from the heavier (higher boiling) oligomers (mainly dimer and trimer). The oligomers may be used as gasoline components but there are limits to the amount of olefin material desirable or allowed in gasoline and it is frequently necessary to hydrogenate the oligomers for use in gasoline. The most desirable component for gasoline blending is $C_8$, e.g., isoctane (2,2,4-trimethyl pentane).

The oligomer may be cracked back to the original olefins and used in cold acid reaction, however, it is not necessary to crack the oligomer which may constitute the olefin feed to cold acid reaction with the isoalkane. As noted above, the result of feeding the oligomers is the same product as if the mono olefin, per se, were fed to the alkylation with the additional benefit of a less exothermic overall alkylation reaction requiring less refrigeration and, hence, a lower energy cost for the alkylation.

The oligomerization process produces a heat of reaction that does not require the magnitude of heat removal as in the cold acid process using mono olefins directly. In fact, when the oligomerization is carried out in a catalytic distillation type reaction, the heat of reaction is removed as boilup, which in this type of reaction is the lower boiling mono olefins and alkanes which are being separated from the oligomer. Thus, even though there is heat produced in the oligomerization, it is of no cost to the production of the gasoline, since the heat is used in the fractionation, and the operating cost of the alkylation unit is reduced by the use of oligomer to replace some or all of the conventional short chain olefin.

In a preferred embodiment of the present alkylation process, a light naphtha stream comprising normal and tertiary olefins (typically a light naphtha from a catalytic cracking unit) is contacted with an acid resin catalyst under oligomerization conditions to preferentially react a portion of the tertiary olefins with themselves to form oligomers, and feeding said oligomers to an alkylation zone with an isoalkane in the presence of an acid alkylation catalyst to produce an alkylation product comprising the alkylate of said tertiary olefin and said isoalkane.

The oligomerization of isoolefins may be carried out in a partial liquid phase in the presence of an acid cation resin catalyst either in straight pass type reaction or in a catalytic distillation reaction where there is both a vapor and liquid phase and a concurrent reaction/fractionation. Preferably, the feed is a $C_4$-$C_5$, $C_4$ or $C_5$ light naphtha cut. The tertiary olefins may include isobutene, and isoamylenes and are more reactive than the normal olefin isomers and are preferentially oligomerized. The primary oligomer products are dimers and trimers. The isoalkanes preferably comprise isobutane, isopentane or mixtures thereof.

When a straight pass reactor is used, such as that disclosed in U.S. Pat. Nos. 4,313,016; 4,540,839; 5,003,124; and 6,335,473, the entire effluent comprising the oligomer, normal olefins and isoalkanes may be fed to an acid alkylation reaction. Additional isobutane is fed to the oligomerization reactor to provide additional a heat sink to remove a portion of the heat of reaction. The normal alkanes are inert under the conditions of the present alkylation. Under alkylation conditions the isoalkane reacts with the normal olefin to form alkylate product and with the individual constituent olefins of the oligomers (i.e., the olefins correspond to those used in the oligomerization) to form the alkylate product. The result of the present process is that the oligomers are dissociated or in some manner make their constituent olefins available for reaction with isoalkanes. Thus, the reaction will produce:
1) isobutene oligomer+isobutane–isooctane;
2) isobutene oligomer+isopentane–branched $C_9$ alkanes;
3) isoamylene oligomer+isobutane–branched $C_9$ alkanes;
4) isoamylene oligomer+isopentane–branched $C_{10}$ alkanes;

whereas it would have been expected that reaction 1) would produce at least or mostly $C_{12}$ alkanes, reaction 2) would produce at least or mostly $C_{13}$ alkanes, reaction 3) would produce at least or mostly $C_{14}$ alkanes, and reaction 4) would produce at least or mostly $C_{15}$ alkanes.

When a catalytic distillation reaction such as that disclosed in U.S. Pat. Nos. 4,242,530 or 4,375,576 is employed for the oligomerization, the oligomer is separated from the lower boiling normal olefins and alkanes in the reaction product by concurrent fractionation. The streams, normal olefins and alkanes (overheads) and oligomers (bottoms), may be united or individually fed to the alkylation or may be used individually with at least the oligomer being fed to the alkylation.

The oligomerization of propylene may be carried out in tubular reactors at 330-482° F. and 1000 to 1215 psig using supported phosphoric acid (sPa), metal complexes (U.S. Pat. Nos. 5,510,555; 4,695,664 and 6,501,001) and various zeolites, especially ZSM-22, ZSM-57 (U.S. Pat. No. 6,143,942) and MCM-22 (U.S. Pat. No. 4,956,514) which has been shown to have favorable characteristics for the oligomerization of propylene at lower pressures and temperatures than the other catalysts.

The feed to the alkylation may comprise one or both the isoolefin oligomers and the propylene oligomers. The present process preferably employs an alkylation unit comprising a downflow reactor packed with contacting internals or packing material (which may be inert or catalytic) through which passes a concurrent multi phase mixture of sulfuric acid, hydrocarbon solvent and reactants at the boiling point of the system. The system comprises a hydrocarbon phase and an acid/hydrocarbon emulsion phase. A significant amount of sulfuric acid is held up on the packing. Reaction is believed to take place between the descending hydrocarbon phase and the sulfuric acid dispersed on the packing. Olefin continuously dissolves into the acid phase and alkylate product is continuously extracted into the hydrocarbon phase. Adjusting the pressure and hydrocarbon composition controls the boiling point temperature. The reactor is preferentially operated vapor-continuous but may also be operated liquid-continuous. The pressure is preferentially higher at the top of the reactor than at the bottom.

Adjusting the flow rates and the degree of vaporization controls the pressure drop across the reactor. Multiple injection of olefin may be used. The type of packing also influences the pressure drop due to the acid phase hold-up. The product mixture before fractionation is the preferred circulating solvent. The acid emulsion separates rapidly from the hydrocarbon liquid and is normally recycled with only a few minutes residence time in the bottom phase separator. Because the products are in essence rapidly extracted from the acid phase (emulsion), the reaction and/or emulsion promoters used in conventional sulfuric acid alkylation processes may be added without the usual concern for breaking the emulsion. The process may be described as hydrocarbon-continuous as opposed to acid-continuous.

Preferably, the disperser comprises a conventional liquid-liquid coalescer of a type which is operative for coalescing vaporized liquids. These are commonly known as "mist eliminators" or "demisters", however, in the present invention the element functions to disperse the fluid materials in the reactor for better contact. A suitable disperser comprises a mesh such as a co-knit wire and fiberglass mesh. For example, it has been found that a 90 needle tubular co-knit mesh of wire and multi-filament fiberglass such as manufactured by Amistco Separation Products, Inc. of Alvin, Tex., can be effectively utilized, however, it will be understood that various other materials such as co-knit wire and multi filament teflon (Dupont™), steel wool, polypropylene, PVDF, polyester or various other co-knit materials can also be effectively utilized in the apparatus. Various wire screen type packings may be employed where the screens are woven rather than knitted. Other acceptable dispersers include perforated sheets and expanded metals, open flow cross channel structures which are co-woven with fiberglass or other materials such as polymers co-knit with the wire mesh expanded or perforated sheets. Additionally the multi-filament component may be catalytic. The multi-filament catalytic material may be polymers, such as sulfonated vinyl resin (e.g., Amberlyst) and catalytic metals such as Ni, Pt, Co, Mo, Ag.

The disperser comprises at least 50 volume % open space up to about 97 volume % open space. Dispersers are positioned within the reaction zone in the reactor. Thus, for example, the multi filament component and the structural element, e.g., knit wire, should comprise about 3 volume % to about 50 volume % of the total disperser, the remainder being open space.

Suitable dispersers include structured catalytic distillation packings which are intended to hold particulate catalysts, or structured distillation packings composed of a catalytically active material, such as that disclosed in U.S. Pat. No. 5,730,843 which is incorporated herein in its entirety and which discloses structures that have a rigid frame made of two substantially vertical duplicate grids spaced apart and held rigid by a plurality of substantially horizontal rigid members and a plurality of substantially horizontal wire mesh tubes mounted to the grids to form a plurality of fluid pathways among the tubes, said tubes being empty or containing catalytic or non catalytic materials; and structured packings which are catalytically inert which are typically constructed of corrugated metal bent at various angles, wire mesh which is crimped, or grids which are horizontally stacked one on top of the other, such as disclosed in U.S. Pat. No. 6,000,685 which is incorporated herein in its entirety and which discloses contact structures comprising a plurality of sheets of wire mesh formed into vee shaped corrugations having flats between the vees, said plurality of sheets being of substantially uniform size having the peaks oriented in the same direction and substantially in alignment, said sheets being separated by a plurality of rigid members oriented normally to and said resting upon said vees.

Other suitable dispersers include: (A) random or dumped distillation packings which are: catalytically inert dumped packings contain higher void fraction and maintain a relatively large surface area, such as, Berl Saddles (Ceramic), Raschig Rings (Ceramic), Raschig Rings (Steel), Pall rings (Metal), Pall rings (Plastic, e.g., polypropylene) and the like and catalytically active random packings which contain at least one catalytically active ingredient, such as Ag, Rh, Pd, Ni, Cr, Cu, Zn, Pt, Tu, Ru, Co, Ti, Au, Mo, V, and Fe as well as impregnated components such a metal-chelate complexes, acids such as phosphoric acid, or bonded, inorganic, powdered materials with catalytic activity; and (B) monoliths which are catalytically inert or active which are structures containing multiple, independent, vertical channels and may be constructed of various materials such as plastic, ceramic, or metals, in which the channels are typically square; however, other geometries could be utilized, being used as such are coated with catalytic materials.

The hydrocarbon feedstock undergoing alkylation by the method of the present invention is provided to the reaction zone in a continuous hydrocarbon phase containing effective amounts of olefinic and isoparaffinic starting materials which are sufficient for forming an alkylate product. The olefin:isoparaffin mole ratio in the total reactor feed should range from about 1:1.5 to about 1:30, and preferably from about 1:5 to about 1:15. Lower olefin:isoparaffin ratios may also be used. Having established a stable operation within these parameters, it is highly desirable to maintain the operating stoichiometric ratios of the olefinic and isoalkane reactants. and thereby maintain the productivity of the alkylation unit at a constant level.

The olefin component should preferably contain 2 to 16 carbon atoms and the isoparaffin component should preferably contain 4 to 12 carbon atoms. Representative examples of suitable isoparaffins include isobutane, isopentane, 3-methylhexane, 2-methylhexane, 2,3-dimethylbutane and 2,4-dimethylhexane. Representative examples of suitable olefins include butene-2, isobutylene, butene-1, propylene, pentenes, ethylene, hexene, octene, and heptene, merely to name a few and as described above may be oligomers of these olefins.

In the fluid process the system uses hydrofluoric or sulfuric acid catalysts under relatively low temperature conditions. For example, the sulfuric acid alkylation reaction is particularly sensitive to temperature with low temperatures being favored in order to minimize the side reaction of olefin polymerization. Petroleum refinery technology favors alkylation over polymerization because larger quantities of higher octane products can be produced per available light chain olefin. Acid strength in these liquid acid catalyzed alkylation processes is preferably maintained at 85 to 94% by weight using the continuous addition of fresh acid and the continuous withdrawal of spent acid. Other acids such as solid phosphoric acid may be used by supporting the catalysts within or on the packing material.

Preferably, the process of the present invention should incorporate relative amounts of acid and hydrocarbon fed to the top of the reactor in a volumetric ratio ranging from about 0.01:1 to about 2:1, and more preferably in a ratio ranging from about 0.05:1 to about 1.5:1. In the most preferred embodiment of the present invention, the ratio of acid to hydrocarbon should range from about 0.1:1 to about 1:1.

Additionally, the dispersion of the acid into the reaction zone should occur while maintaining the reactor vessel at a temperature ranging from about 0° F. to about 200° F., and more preferably from about 15° F. to about 130° F. Similarly, the pressure of the reactor vessel should be maintained at a level ranging from about 0.5 ATM to about 50 ATM, and more preferably from about 0.5 ATM to about 20 ATM. Most preferably, the reactor temperature should be maintained within a range from about 15° F. to about 110° F. and the reactor pressure should be maintained within a range from about 0.5 ATM to about 5 ATM.

In general, the particular operating conditions used in the process of the present invention will depend to some degree upon the specific alkylation reaction being performed. Process conditions such as temperature, pressure and space velocity as well as the molar ratio of the reactants will affect the characteristics of the resulting alkylate product and may be adjusted in accordance with parameters known to those skilled in the art.

An advantage of operating at the boiling point of the present reaction system is that there is some evaporation which aids in dissipating the heat of reaction and making the temperature of the incoming materials closer to that of the materials leaving the reactor as in an isothermal reaction.

Once the alkylation reaction has gone to completion, the reaction mixture is transferred to a suitable separation vessel where the hydrocarbon phase containing the alkylate product and any unreacted reactants is separated from the acid. The typical density for the hydrocarbon phase ranges from about 0.6 g/cc to about 0.8 g/cc and since densities for the acid generally fall within the ranges of about 0.9 g/cc to about 2.0 g/cc. The two phases are preferably separable by a conventional distillation, which provides a reusable isoalkane.

Referring now to the FIGURE a description of the invention is presented showing an oligomerization reactor 10 containing the oligomerization catalyst. The olefins are fed via flow line 101. Isobutane is fed via line 102 to provide an additional heat sink to remove a portion of the heat of reaction generated during the oligomerization. The effluent 103 from the oligomerization reactor is fed to the alkylation unit 20 where substantially all of the olefins are reacted with isobutane to produce the alkylate. Make up isobutane is added as needed via flow line 107. If the olefins in the feed are higher stoichiometrically than the isobutane then make up isobutane is added via flow line 107. A by pass line 108 allows for a portion of the isobutane feed to bypass the oligomerization reactor 10 and be fed directly to the alkylation unit 20. The effluent from the alkylation unit in flow line 104 is fed to a distillation column 30 which may be a debutanizer, deisobutanizer or a simple stripper, which removes the unreacted $C_4$'s as overheads in flow line 106. The alkylate product is removed as bottoms via flow line 105. The $C_4$'s in flow line 106 are combined with the make up isobutane and fed to the oligomerization reactor 10. If desired a side draw (not shown) of normal butane can be taken from the distillation column 30 to prevent build up in the system.

Due to the different conditions for oligomerization for propylene and the isoolefins, an optional propylene oligomerization reactor 10a with catalyst and conditions favoring propylene oligomerization may be employed with propylene fed via line 101a and the oligomer recovered in line 103a which is conveniently combined with isoolefin oligomer in line 103 for feed to the alkylation unit 20.

Optionally a flow line 110 is provided to give flexibility to adjust the overall isobutane to olefin ratio for the production of alkylate. If the olefins are lower stoichiometrically than isobutane in the feed stream then a draw may be taken from the recycle via line 110.

Optionally isobutane may be drawn off and passed via line 111 to a dehydrogenation unit 40 to adjust the overall balance via dehydrogenation of the isobutane to isobutene. Regular feed to the dehydrogenation unit 40 is a mixture of normal and isobutane in flow line 109. In this embodiment an isobutene rich stream is removed via flow line 111 and fed into the oligomerization unit 10 along with the other olefin feed in flow line 101.

In one embodiment the olefinic feed to the oligomerization reactor 10 is totally or predominately derived from dehydrogenation unit 40 with the elimination or substantial reduction in the olefinic feed through line 101.

In another option, a portion of the effluent from the oligomerization reactor 10 in flow line 103 may be spilled back to the reactor via flow line 112 for further oligomerization.

The invention claimed is:

1. A process for the alkylation of isoalkane with olefins, the process comprising:
    feeding isoalkane and $C_3$ to $C_5$ olefins comprising an isoolefin to an oligomerization unit;
    reacting the olefins with themselves in the oligomerization unit to produce oligomers of said olefins;
    contacting said oligomers with isoalkane in an alkylation unit under alkylation conditions to produce alkylate product corresponding to the reaction of said olefins and said isoalkane; and
    adjusting the feed of the isoalkane to the oligomerization unit to adjust the ratio of olefins to isoalkane in said alkylation unit.

2. The process according to claim 1 wherein said oligomers comprise propylene oligomers and isoolefin oligomers.

3. The process of claim 1, further fractionally distilling the alkylation product in a distillation column to recover unreacted isoalkane from the alkylate product.

4. The process according to claim 3 wherein the ratio of the isoolefins to isoalkane is adjusted by at least one of: (1) recycling said recovered unreacted isoalkane to the oligomerization unit; (2) adding fresh isoalkane to the recovered unreacted isoalkane for recycle to the oligomerization unit; (3) dehydrogenation of a portion of (a) the recovered unreacted isoalkane or (b) the unreacted isoalkane and the fresh isoalkane to produce an isoolefin product which is added to the oligomerization unit; and (4) a combination thereof.

5. The process according to claim 4 wherein the ratio of the isoolefins to isoalkane is adjusted by adding isoalkane to the recovered unreacted isoalkane for recycle to the oligomerization unit.

6. The process according to claim 4 wherein the ratio of the isoolefins to isoalkane is adjusted by dehydrogenation of a portion of at least one of: (a) the recovered unreacted isoalkane and (b) the unreacted isoalkane and the fresh isoalkane to produce an isoolefin product which is added to the oligomerization unit.

7. The process according to claim 4 wherein the ratio of the isoolefins to isoalkane is adjusted by adding isoalkane to the recovered unreacted isoalkane for recycle to the oligomerization unit and by dehydrogenation of a portion of the recovered unreacted isoalkane to an isoolefin product which is added to the oligomerization unit.

8. A process for the alkylation of isobutane with olefins comprising the steps of:
    (a) feeding a first stream containing $C_3$-$C_5$ olefins to an oligomerization reaction wherein the isoolefins contained with the first stream react with themselves and each other to produce $C_5$ and higher oligomers;
    (b) feeding a second stream containing isoalkanes comprising at least one of isobutane and isopentane to the oligomerization reaction and adjusting the feed of the isoalkanes to the oligomerization reaction to adjust a ratio of the olefins and the isoalkane in an alkylation reaction;
    (c) feeding the effluent from the oligomerization reaction to the alkylation reaction where the oligomers react with isobutane, isopentane or mixtures thereof to produce alkylate; and
    (d) feeding the effluent from the alkylation to a distillation wherein unreacted isobutane is removed as overheads and alkylate is removed as bottoms.

9. The process according to claim 8 wherein the overheads are recycled to said second stream.

10. The process according to claim 8 wherein a portion of the overheads are withdrawn.

11. The process according to claim 10 wherein the withdrawn portion of the overheads containing isobutane is fed to a dehydrogenation unit where a portion of the isobutane is converted to isobutene and fed to the oligomerization reaction.

12. The process according to claim 8 wherein a portion of said second stream bypasses the oligomerization reaction and is fed directly to the alkylation reaction.

13. The process according to claim 8 wherein a portion of the effluent from the oligomerization reaction, including oligomers, is recycled as feed to the oligomerization reaction.

14. The process according to claim 8 comprising: feeding a portion of the effluent from the oligomerization reaction to an alkylation reaction where the oligomers react with isobutane to produce alkylate and feeding a portion of the effluent from the oligomerization reaction, including oligomers, back to the oligomerization reaction.

15. The process according to claim 8 comprising: recycling a portion of said overheads to said oligomerization reaction; feeding a portion of said overheads to a dehydrogenation unit wherein a portion of the isobutane contained within said overheads is converted to isobutene; and feeding the isobutenes from said dehydrogenation unit to said oligomerization reaction.

* * * * *